United States Patent
Moon et al.

(10) Patent No.: US 7,820,982 B2
(45) Date of Patent: Oct. 26, 2010

(54) GRID FOR TRANSMISSION ELECTRON MICROSCOPY TOMOGRAPHY AND METHOD OF FABRICATING THE SAME

(75) Inventors: Won Jin Moon, Gwangju (KR); Byung Kyu Park, Gwangju (KR); Youn Joong Kim, Daejeon (KR); Jee Young Lee, Chungcheongnam-do (KR); Sang Hee Lee, Daejeon (KR); Dong Sik Bae, Gyeongnam (KR)

(73) Assignee: Korea Basic Science Institute, Daejeon (KR)

( * ) Notice: Subject to any disclaimer, the term of this patent is extended or adjusted under 35 U.S.C. 154(b) by 127 days.

(21) Appl. No.: 12/170,670

(22) Filed: Jul. 10, 2008

(65) Prior Publication Data

US 2009/0065708 A1    Mar. 12, 2009

(30) Foreign Application Priority Data

Sep. 11, 2007    (KR) .................. 10-2007-0092240

(51) Int. Cl.
*H01J 37/00* (2006.01)
(52) U.S. Cl. .................. 250/440.11; 250/311

(58) Field of Classification Search ............ 250/440.11, 250/311
See application file for complete search history.

(56) References Cited

U.S. PATENT DOCUMENTS

| | | | |
|---|---|---|---|
| 7,194,122 B2 | 3/2007 | Faber et al. | |
| 7,348,570 B2 * | 3/2008 | Allred et al. | ........... 250/440.11 |
| 7,366,279 B2 | 4/2008 | Edic et al. | |
| 2004/0057556 A1 | 3/2004 | Luhta et al. | |

\* cited by examiner

*Primary Examiner*—Kiet T Nguyen
(74) *Attorney, Agent, or Firm*—Lucas & Mercanti, LLP

(57) ABSTRACT

Disclosed is a moon grid for transmission electron microscopy tomography, including a mesh sheet for protecting an upper objects and a support film formed on the mesh sheet and having nanoparticles dispersed throughout, in which the nanoparticles dispersed throughout the support film are used as reference points in the reconstruction of two-dimensional transmission electron microscopy images into a three-dimensional image, thus omitting a process of attaching markers in the course of preparation of a sample and easily forming reference points even on a sample to which it is impossible to attach markers. A method of fabricating such a moon grid is also provided.

4 Claims, 4 Drawing Sheets

GRID FOR TRANSMISSION ELECTRON MICROSCOPY TOMOGRAPHY AND METHOD OF FABRICATING THE SAME

CROSS-REFERENCES TO RELATED APPLICATION

This patent application claims the benefit of priority under 35 U.S.C. §119 from Korean Patent Application No. 10-2007-0092240 filed on Sep. 11, 2007, the contents of which are incorporated herein by reference.

BACKGROUND OF THE INVENTION

1. Field of the Invention

The present invention relates to a moon grid for transmission electron microscopy tomography and preparation method thereof, and, more particularly, to a moon grid for transmission electron microscopy tomography, which comprises a mesh sheet for protecting an upper objects and a support film formed on the mesh sheet and having nanoparticles dispersed throughout and preparation method thereof.

2. Description of the Related Art

Transmission electron microscopy (TEM) is considered to be the most common tool for studying materials and biomedical materials on a nano scale.

Because the TEM is generally used to observe 2D images formed by electrons transmitted through a sample, the spatial resolution thereof is as sharp as about 0.1 nm.

However, information about the sample in the thickness direction causes problems in which the shadow of an object positioned on the electrons in a traveling direction overlaps underlying objects, or information of objects on top overlaps the information of underlying objects. In this case, it is difficult to correctly analyze overlapping information.

In order to solve or mitigate the above problems, recently, TEM tomography or STEM tomography is developed using a CT (Computed Tomograph) in the medical field, and further, the application range thereof is widened not only to the 3D structural analysis of amorphous materials, polymeric materials (chemical materials) and biomedical materials, but also to the short circuit analysis of semiconductors.

The procedure of obtaining a 3D image of a sample using TEM tomography or STEM tomography is briefly described below.

First, a thin film sample for TEM tomography is prepared. The preparation of the thin film sample may be conducted using any one process selected from among ultramicrotomy, dispersion, and FIB (Pick-up, micro-sampling). In the case where the biomedical or polymeric thin film sample is prepared through ultramicrotomy, dyeing may be performed.

The thin film sample is attached to a grid, and markers are also attached thereto.

The grid to which the thin film sample and markers are attached is placed in the TEM holder for TEM tomography or STEM tomography, and is then photographed, thus obtaining 2D images. As such, the respective 2D images are obtained by continuously tilting the thin film sample.

The 2D images are processed using a computer and are thus reconstructed into a 3D image.

As such, reconstruction of the 2D images into the 3D image is realized using the attached markers as reference points.

In this way, the markers play an important role in reconstructing the 2D images into the 3D image, and thus, depending on whether the size, number, and distribution of the attached markers are appropriate, the resolution of TEM tomography or STEM tomography, and even the success or failure of TEM tomography or STEM tomography, may be determined.

Further, a lot of time and effort are required to set conditions for the attachment of the markers depending on the type of thin film sample. In some cases, the markers fail to be attached. That is, attributable to reasons such as excessive attachment of the markers and so on, problems in which the thin film sample is hidden or attachment of the markers fails occur.

Because the above work greatly hinders efficient TEM tomography or STEM tomography and consumes unnecessary time, the procedure of attaching the markers needs to be improved in order to accomplish high efficiency.

Therefore, the present inventors, researching for solving the above disadvantages and problems encountered in the related art, have prepared a moon grid for TEM tomography, comprising a mesh sheet for protecting an upper structure and a support film formed on the mesh sheet and having nanoparticles dispersed throughout, and found that the moon grid for TEM tomography does not need for the additional attachment of markers in the course of preparation of a sample, thereby efficiently create a 3D image. Based on this finding, the present invention was completed.

SUMMARY OF THE INVENTION

Accordingly, an object of the present invention is to provide the moon grid for TEM tomography, eliminating the need for the additional attachment of markers in the course of preparation of a sample, thereby efficiently creating a 3D image.

The other object of the present invention is to provide a preparation method of the moon grid for TEM tomography.

In order to accomplish the above objects, the present invention provides a moon grid for TEM tomography, comprising a mesh sheet for protecting an upper structure; and a support film formed on the mesh sheet and having nanoparticles dispersed throughout, wherein the nanoparticles are used as reference points in reconstruction of 2D images into a 3D image.

In addition, the present invention provides a preparation method of a moon grid for TEM tomography, comprising mixing powder for a support film with chloroform, thus preparing a mixture solution for a support film (step 1); blending the mixture solution with a predetermined amount of nanoparticles, and then sonicating the mixture solution so that the nanoparticles are dispersed throughout the mixture solution (step 2); dipping a glass substrate into the mixture solution having the nanoparticles dispersed throughout (step 3); taking the glass substrate out of the mixture solution at a predetermined rate, and then naturally drying the glass substrate, thus forming a support film having the nanoparticles dispersed throughout on the surface of the glass substrate (step 4); and separating the support film from the glass substrate, and then disposing a mesh sheet on the support film, thus forming the moon grid for TEM tomography (step 5).

BRIEF DESCRIPTION OF THE MARK OF DRAWINGS

Figure 1:
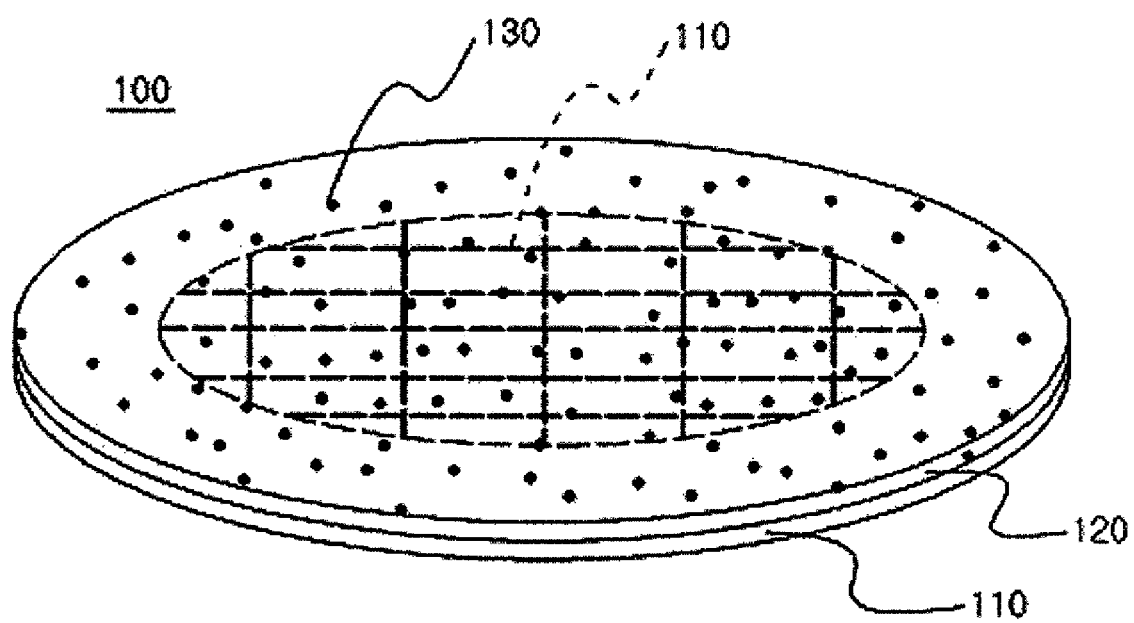
FIG. 1 is a perspective view illustrating the moon grid for TEM tomography, according to the present invention.

100: moon grid for TEM tomography
110: mesh sheet
120: support film
130: nano particle

DESCRIPTION OF THE PREFERRED EMBODIMENTS

The present invention provides a moon grid for TEM tomography.

The moon grid for TEM tomography according to the present invention may comprise a mesh sheet for protecting an upper objects and a support film formed on the mesh sheet and having nanoparticles dispersed throughout.

In the present invention, the nanoparticles are used as reference points or markers in the subsequent course of reconstruction of 2D TEM images into a 3D image. Hence, the nanoparticles have an average particle size of 3~200 nm, and preferably have a size and are made of a material so as to make it possible to remain as markers on the 2D TEM images.

For instance, the nanoparticles may have a predetermined shape, including a spherical shape or a polyhedral shape, such as an octahedral shape, and may comprise an amorphous material or a crystalline material having a density higher than the density of magnesium (1.783 g/cm$^3$). Specific examples of the material for the nanoparticles include amorphous silica, crystalline gold particles, silver, platinum, alumina, and α-Fe$_2$O$_3$. This is because the nanoparticles only remain as markers having a predetermined shape on the 2D images.

In addition, the present invention provides a preparation method of the moon grid for TEM tomography.

The preparation method according to the present invention comprises:

mixing powder for a support film with chloroform, thus preparing a mixture solution for a support film (step 1);

blending the mixture solution with a predetermined amount of nanoparticles, and then sonicating the mixture solution so that the nanoparticles are dispersed throughout the mixture solution (step 2);

dipping a glass substrate into the mixture solution having the nanoparticles dispersed throughout (step 3);

taking the glass substrate out of the mixture solution at a predetermined rate, and then naturally drying the glass substrate, thus forming a support film having the nanoparticles dispersed throughout on the surface of the glass substrate (step 4); and separating the support film from the glass substrate, and then disposing a mesh sheet on the support film, thus forming the moon grid for TEM tomography (step 5).

As the moon grid for TEM tomography according to the present invention, which is prepared by above-mentioned method, has markers prior to attaching the sample, problems of prior art when TEM tomography is conducted, for example, in a series of steps of preparing a sample, preparing a grid, attaching the sample on the grid, attaching markers on the grid having the attached sample, acquiring images from various angles, and reconstructing such images into a 3D image, the sample and markers are sequentially attached on the grid before the images are acquired from various angles, whereby a lot of time and effort are required to set the conditions for attachment of the markers depending on the type of sample, and furthermore, in some cases, the attachment of the markers may fail, resulting in inefficient tomography, etc., can be solved.

These aspects, technical advantages, and functional effects of the present invention will become apparent and more readily appreciated from the following description of the preferred embodiments, taken in conjunction with the accompanying drawings. In the description, like reference numerals refer to like elements.

FIG. 1 is a perspective view illustrating the moon grid for TEM tomography, according to the present invention.

As seen in FIG. 1, the moon grid 100 for TEM tomography according to the present invention includes a mesh sheet 110 and a support film 120.

The support film 120 has nanoparticles 130 dispersed throughout. That is, the nanoparticles 130 are uniformly dispersed in and on the support film 120. When observed with TEM, the nanoparticles 130 are uniformly displayed at a predetermined size.

The nanoparticles 130 have an average particle size of 3~200 nm, and preferably 20~100 nm, depending on the observation magnification.

For the nanoparticles 130, any material may be used as long as it has a predetermined shape, including a spherical shape or a polyhedral shape, such as an octahedral shape, and a predetermined size. This is because the nanoparticles 130 only remain as markers having a predetermined shape on the 2D images. Further, any material may be used for the nanoparticles as long as it is an amorphous material or a crystalline material having a density higher than the density of magnesium (1.783 g/cm$^3$), while satisfying the above conditions. Examples of the material for the nanoparticles include amorphous silica, crystalline gold particles, silver, platinum, alumina, and α-Fe$_2$O$_3$.

The size, shape, and material of the nanoparticles 130 may vary with the type of sample.

In a moon grid for TEM tomography according to the invention, the support film 120 may be any one film of Formvar, Collodion, and Butvar.

In a moon grid for TEM tomography according to the invention, the mesh sheet 110 is a structure for supporting the moon grid 100 for TEM tomography, and the size thereof may be determined by the size of the sample.

The mesh sheet 110 may have a variety of mesh numbers, such as 50, 75, 100, 150, 200, etc. The mesh number of the mesh sheet 110 is preferably selected such that it is smaller than the size of the sample and is larger than the size of the nanoparticles 130. The reason is that the field of view must not be obstructed when obtaining the 2D images from various angles with respect to the area of the sample to be observed.

The outer diameter of the mesh sheet 110 may have various sizes (e.g., 2 mm or 3 mm), and is set to be suitable for the inner diameter of the sample stage of the TEM holder. In addition, the mesh sheet may be cut into ½ or ⅔ before use, as necessary.

The material for the mesh sheet 110 may be selected from among Cu, Ni, Au, Pt, and Mo.

In the moon grid 100 for TEM tomography according to the present invention, the nanoparticles 130 are uniformly dispersed in and on the support film 120, and thus the sample is attached on the moon grid 100 for TEM tomography (particularly, on the surface of the support film 120), after which the moon grid 100 for TEM tomography is placed in a transmission electron microscope and is then observed from various angles, thereby acquiring multiple 2D images in which the sample and the nanoparticles 130 are displayed as the sample image and the markers, respectively. Thereafter, such 2D images are reconstructed into a 3D image using the markers as reference points.

The sample on the moon grid 100 for TEM tomography placed in the transmission electron microscope is acquired in the form of the multiple 2D images while the observation angle thereof is uniformly varied in a predetermined range (from +60° to −60°).

Figure 2:
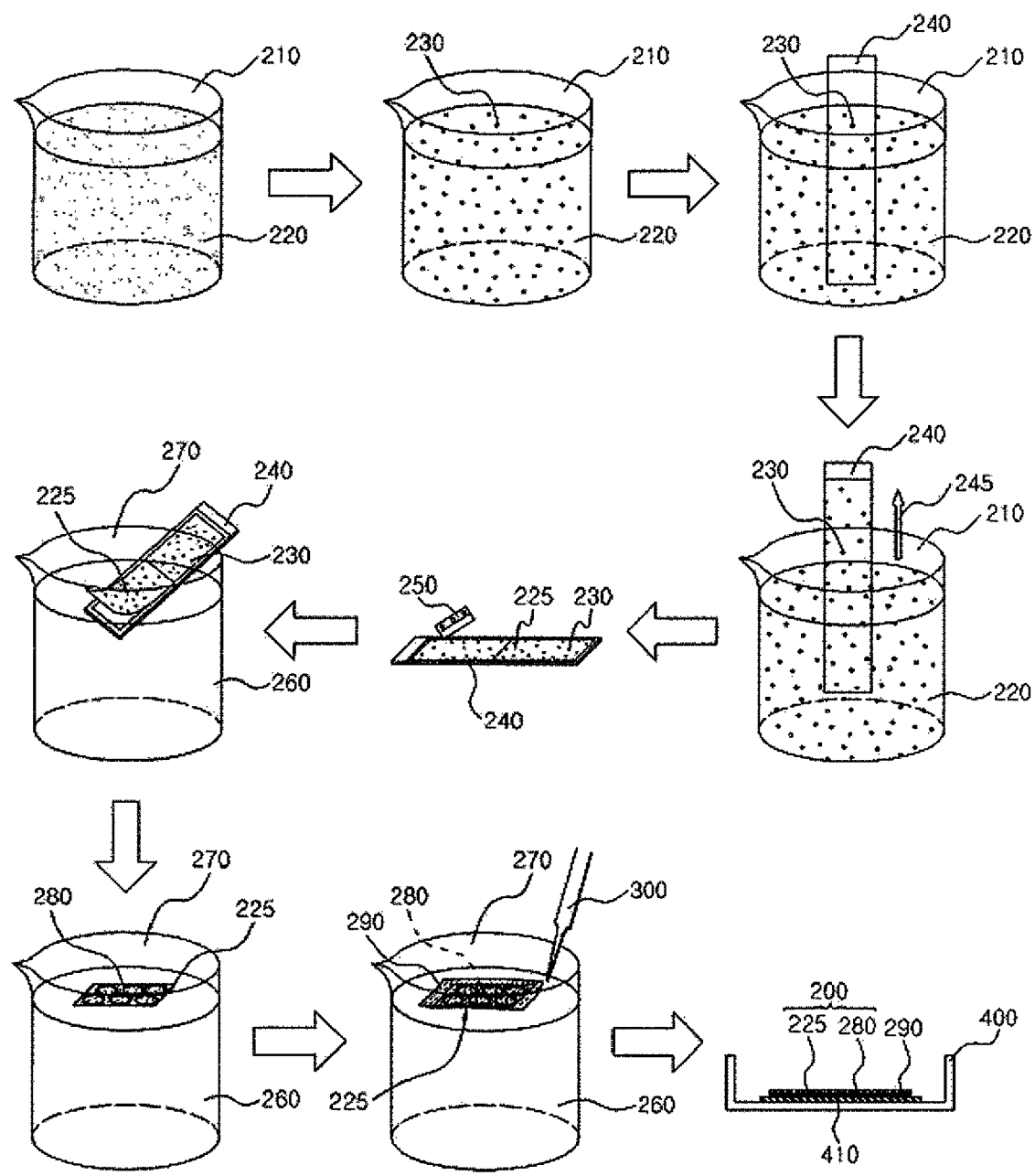
FIG. 2 is a schematic view illustrating the process of fabricating the moon grid for TEM tomography, according to the present invention.

FIG. 2 illustrates the process of fabricating the moon grid for TEM tomography according to the present invention.

As seen in FIG. 2, powder for a support film and chloroform are mixed together in a beaker 210, thus preparing a mixture solution 220 for a support film.

The powder for a support film may be any one selected from among Formvar powder, Collodion powder, and Butvar powder.

In the present invention, the mixture solution 220 for a support film is prepared using Formvar powder. The method of preparing the mixture solution 220 for a support film includes mixing Formvar powder with chloroform, thus preparing a 0.3% mixture solution for a Formvar support film.

Subsequently, the mixture solution 220 for a support film is mixed with nanoparticles 230.

Preferably, the nanoparticles 230 are spherical amorphous particles have an average particle size of 3~200 nm and high specific gravity. For the nanoparticles 230, any material may be used as long as it can be photographed by the TEM such that the nanoparticles 230 are used as the markers on the TEM images. In the present invention, the nanoparticles 230 are exemplified by spherical amorphous silica.

The mixture solution 220 blended with the nanoparticles 230 is sonicated so that the nanoparticles 230 are uniformly dispersed throughout the mixture solution 220 for a support film.

Although sonication is not shown in the drawing, a sonicator may be used. Specifically, the beaker 210 containing the mixture solution 220 blended with the nanoparticles 230 is placed in the sonicator, after which the beaker 210 is sonicated for a predetermined period of time, thereby uniformly dispersing the nanoparticles 230 throughout the mixture solution 220.

Subsequently, a glass substrate 240 is dipped into the mixture solution 220 for a support film, having the nanoparticles 230 dispersed throughout.

Subsequently, the glass substrate 240 is taken out of the mixture solution 220 for a support film at a predetermined rate 245.

The rate at which the glass substrate 240 is taken out is set to be 1~10 cm/min.

The glass substrate 240 is removed from the beaker in a state in which the mixture solution 220 for a support film and the nanoparticles 230 dispersed throughout the mixture solution 220 for a support film are adhered to the surface of the glass substrate.

The glass substrate 240 is naturally dried, thus preparing a support film 225 having the nanoparticles 230 dispersed throughout.

Figure 3:
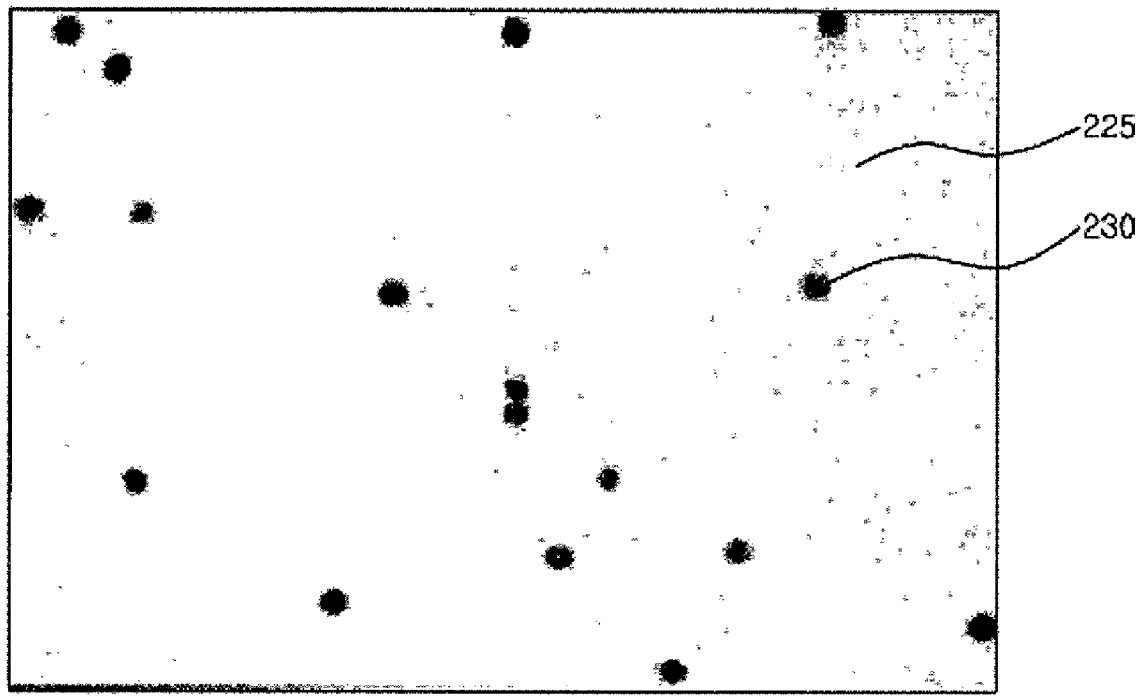
FIG. 3 is a TEM image illustrating the support film having nanoparticles dispersed throughout, according to the present invention.

As shown in the photograph of FIG. 3, the nanoparticles 230 are dispersed throughout the support film 225. (FIG. 3 is a TEM image of the support film 225 having the nanoparticles 230 dispersed throughout.)

Subsequently, the support film 225 is cut to have a predetermined size, using a cutting member 250 such as a razor blade or a knife.

Subsequently, the glass substrate 240 is placed in another beaker 270 containing distilled water 260, such that the support film 225 having a predetermined size is separated from the glass substrate 240 to thus float on the surface of the distilled water 260.

Subsequently, one or more mesh sheets 280 are disposed on the support film 225 floating on the surface of the distilled water 260.

The mesh sheet 280 is a structure for supporting the moon grid 100 for TEM tomography, and the size thereof may be determined by the size of the sample. Specifically, the mesh number of the mesh sheet 280 should be large enough that the field of view is not obstructed when obtaining the 2D images from various angles with respect to the area of the sample to be observed.

Subsequently, a para film 290 is disposed on the support film 225 having the mesh sheets 280 thereon.

As such, the para film 290 functions to protect the mesh sheets 280 and the support film 225 when the mesh sheets and support film are taken out of the distilled water 260.

Subsequently, a moon grid body 200 for TEM tomography, including the support film 225 and the mesh sheets 280, and the pare film 290 for protecting the moon grid body 200 are taken out of the distilled water 260 using a pair of tweezers.

Subsequently, the moon grid body 200 for TEM tomography is transferred into an evaporating dish 400 and is then naturally dried.

As such, filter paper 410 is first provided in the evaporating dish 400 to facilitate the downward flow of distilled water from the moon grid body 200 for TEM tomography.

Subsequently, although not shown in FIG. 2, the moon grid body 200 for TEM tomography is separated from the para film 290, thereby completing the moon grid 100 for TEM tomography shown in FIG. 1.

Figure 4:
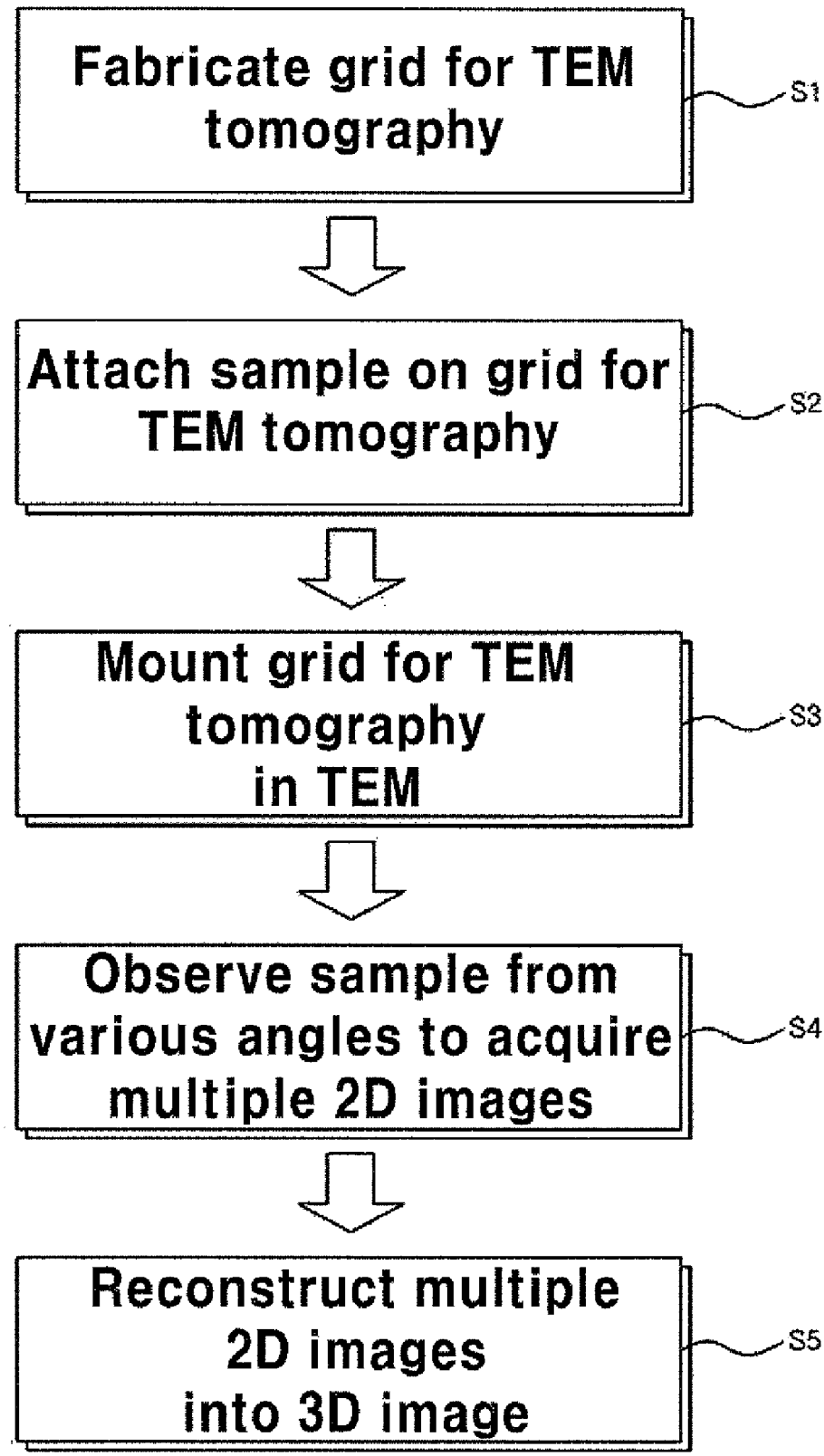
FIG. 4 is a flowchart illustrating the process of acquiring a 3D TEM image using the moon grid for TEM tomography fabricated according to the present invention.

FIG. 4 is a flowchart illustrating the process of acquiring a 3D TEM image using the moon grid for TEM tomography fabricated as above.

As seen in FIG. 4, the moon grid for TEM tomography is fabricated through the process of FIG. 2 (S1).

Subsequently, the sample is attached on the moon grid for TEM tomography (S2).

As such, the moon grid for TEM tomography is composed of the mesh sheet, the support film having nanoparticles dispersed throughout, and the sample, which are sequentially disposed.

Subsequently, the moon grid for TEM tomography is placed and mounted in a transmission electron microscope (S3).

Subsequently, the sample mounted in the transmission electron microscope is observed from various angles, thus acquiring multiple 2D images (S4).

As such, the 2D images are obtained by observing the sample attached on the moon grid for TEM tomography while varying the observation angle in the range from +60° to −60°.

The 2D images thus acquired include not only the image of the sample but also the nanoparticles dispersed throughout the support film of the moon grid for TEM tomography, which are present as the markers.

Subsequently, the 2D images are reconstructed into a 3D image using a computer (S5).

As such, reconstruction of the 2D images into the 3D image is realized using the markers shown on the 2D images as reference points, wherein the markers are the image of the nanoparticles 230 as shown in FIG. 3.

Therefore, the present invention provides the moon grid for TEM tomography and the method of fabricating the same. Specifically, the moon grid for TEM tomography, including the mesh sheet and the support film having nanoparticles dispersed throughout, and the method of fabricating the moon grid for TEM tomography are provided, thereby facilitating the imaging of an amorphous sample, a biomedical sample, and a chemical sample, which are conventionally difficult to obtain as a 3D TEM image. Further, because the nanoparticles, serving as markers, are already dispersed throughout the support film, the process of attaching the markers can be omitted after the attachment of the sample, thus simplifying the experimental procedure.

According to the present invention, in the moon grid for TEM tomography and the fabrication method thereof, a conventional process of preparing a sample for tomography is simplified, thus realizing efficient tomography.

Furthermore, in the case where the sample is an amorphous sample, a chemical sample, and a biomedical sample, a conventional grid is disadvantageous in that markers are difficult to attach thereto, thus making it almost impossible to obtain a 3D image, but the moon grid for TEM tomography according to the present invention can overcome the above disadvantage because it is already provided with markers before the attachment of the sample.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A grid for transmission electron microscopy tomography, comprising:
    a mesh sheet for protecting an upper objects; and
    a support film formed on the mesh sheet and having nanoparticles dispersed throughout,
    wherein the nanoparticles are used as reference points in reconstruction of two-dimensional images into a three-dimensional image.

2. The grid as set forth in claim 1, wherein the nanoparticles have an average particle size of 3~200 nm.

3. The grid as set forth in claim 1 or 2, wherein the nanoparticles have a spherical shape or a polyhedral shape.

4. The grid as set forth in claim 3, wherein the nanoparticles comprise an amorphous material or a crystalline material having a density higher than a density of magnesium (1.783 g/cm$^3$).

* * * * *